(12) United States Patent
Holleboom

(10) Patent No.: US 6,691,553 B2
(45) Date of Patent: Feb. 17, 2004

(54) GAS SENSOR PROTECTIVE SHIELD

(75) Inventor: Bruce William Holleboom, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 247 days.

(21) Appl. No.: 09/911,275

(22) Filed: Jul. 23, 2001

(65) Prior Publication Data

US 2002/0040599 A1 Apr. 11, 2002

Related U.S. Application Data

(60) Provisional application No. 60/228,678, filed on Aug. 29, 2000.

(51) Int. Cl.⁷ .............................................. G01N 27/46
(52) U.S. Cl. ..................................................... 73/23.32
(58) Field of Search ............................ 73/23.31–23.33, 73/118.1; 204/409–411, 424–429

(56) References Cited

U.S. PATENT DOCUMENTS

| | | | |
|---|---|---|---|
| 4,040,930 A | * | 8/1977 | Dillon |
| 4,111,778 A | * | 9/1978 | Davis et al. |
| 4,240,890 A | * | 12/1980 | Watanabe et al. |
| 4,265,724 A | * | 5/1981 | Haecker et al. |
| 4,588,493 A | * | 5/1986 | Blumenthal et al. |
| 4,591,423 A | * | 5/1986 | Kato et al. |
| 4,784,728 A | * | 11/1988 | Capone |
| 4,986,892 A | * | 1/1991 | Kato et al. |
| 5,619,493 A | | 4/1997 | Ritz et al. |
| 5,689,059 A | * | 11/1997 | Oh et al. .................... 73/23.31 |
| 5,817,920 A | * | 10/1998 | Kuisell et al. ............. 73/23.31 |
| 6,182,498 B1 | * | 2/2001 | Mizutani et al. ........... 73/23.32 |

* cited by examiner

Primary Examiner—Robert Raevis
(74) Attorney, Agent, or Firm—Jimmy L. Funke

(57) ABSTRACT

One embodiment of a gas sensor shield comprises: an elongated body comprising solid sides and a tip disposed across one end of said shield; and an opening disposed within said tip, wherein said opening comprises at least two elongated apertures.

16 Claims, 2 Drawing Sheets

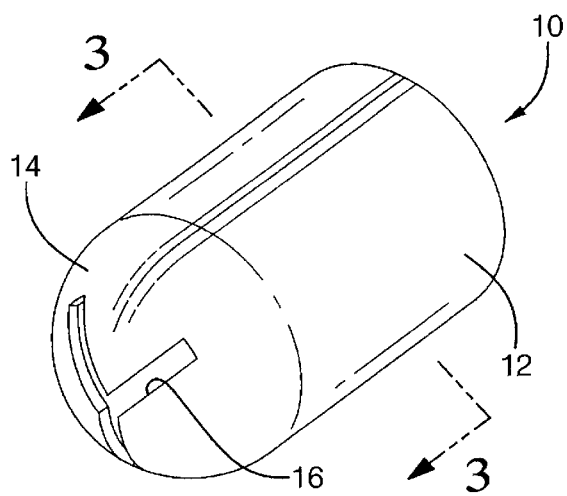
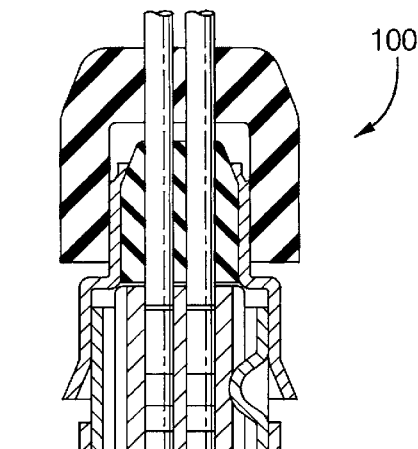
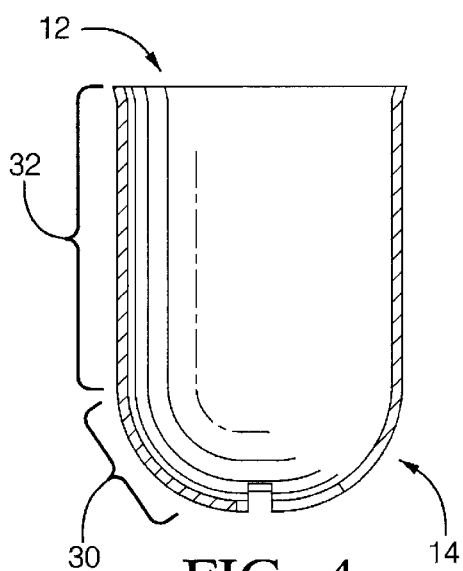
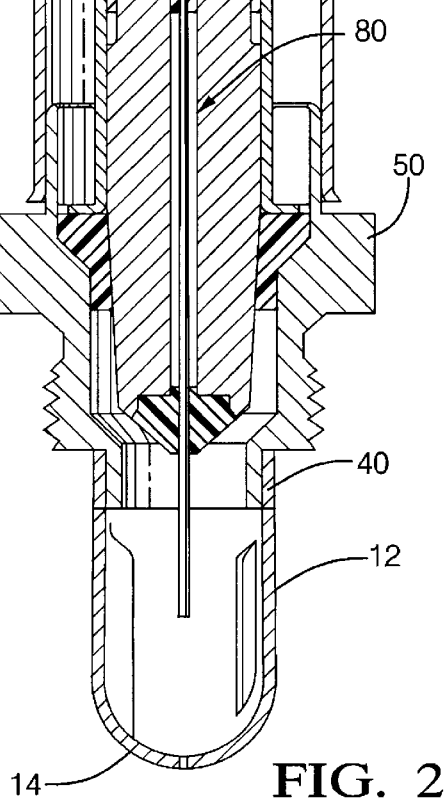

GAS SENSOR PROTECTIVE SHIELD

CROSS REFERENCE TO RELATED APPLICATIONS

This application claims the benefit of U.S. Provisional Application Ser. No. 60/228,678, filed on Aug. 29, 2000, which is hereby incorporated herein by reference.

BACKGROUND OF INVENTION

Oxygen sensors are used in a variety of applications that require qualitative and quantitative analysis of gases. In automotive applications, the direct relationship between oxygen concentration in the exhaust gas and air to fuel ratio (A/F) of the fuel mixture supplied to the engine allows the oxygen sensor to provide oxygen concentration measurements for determination of optimum combustion conditions, maximization of fuel economy, and management of exhaust emissions.

One type of sensor uses an ionically conductive solid electrolyte between porous electrodes. For oxygen sensing, solid electrolyte sensors are used to measure oxygen activity differences between an unknown gas sample and a known gas sample. In the use of a sensor for automotive exhaust, the unknown gas is exhaust and the known gas, (i.e., reference gas), is usually atmospheric air because the oxygen content in air is relatively constant and readily accessible. This type of sensor is based on an electrochemical galvanic cell operating in a potentiometric mode to detect the relative amounts of oxygen present in an automobile engine's exhaust. When opposite surfaces of this galvanic cell are exposed to different oxygen partial pressures, an electromotive force ("emf") is developed between the electrodes according to the Nernst equation.

With the Nernst principle, chemical energy is converted into electromotive force. A gas sensor based upon this principle typically consists of an ionically conductive solid electrolyte material, a porous electrode with a porous protective overcoat exposed to exhaust gases ("exhaust gas electrode"), and a porous electrode exposed to a known gas' partial pressure ("reference electrode"). Sensors typically used in automotive applications use a yttrium stabilized zirconia based electrochemical galvanic cell with porous platinum electrodes, operating in potentiometric mode, to detect the relative amounts of a particular gas, such as oxygen for example, that is present in an automobile engine's exhaust. Also, a typical sensor has a ceramic heater attached to help maintain the sensor's ionic conductivity. When opposite surfaces of the galvanic cell are exposed to different oxygen partial pressures, an electromotive force is developed between the electrodes on the opposite surfaces of the zirconia wall, according to the Nernst equation:

$$E = \left(\frac{RT}{4F}\right) \ln\left(\frac{P_{O_2}^{ref}}{P_{O_2}}\right)$$

Due to the large difference in oxygen partial pressure between fuel rich and fuel lean exhaust conditions, the electromotive force (emf) changes sharply at the stoichiometric point, giving rise to the characteristic switching behavior of these sensors. Consequently, these potentiometric oxygen sensors indicate qualitatively whether the engine is operating fuel-rich or fuel-lean, conditions without quantifying the actual air-to-fuel ratio of the exhaust mixture. Oxygen sensors measure all of the oxygen present in the exhaust to make the correct determination when the oxygen content (air) exactly equals the hydrocarbon content (fuel).

Oxygen sensors include a ceramic sensing element that is brought up to temperature by a heater. The heated sensing element is sensitive to water in the exhaust system. Traditionally, heated oxygen sensors have been subject to internal ceramic element cracking, especially in sensors disposed down stream from the catalytic converter, induced by condensate water in the exhaust. Water enters a vehicle's exhaust system, including the gas sensor, due to condensation of combustion byproducts. As a result, the heated sensing element may be subject to ceramic cracking when the water contacts the hot element. The sudden impact of liquid water will cause severe thermal shock and cracking of the element, causing irreparable damage to the sensor. The problem has been sought to be rectified through special protective shields in the exhaust system or changes in the exhaust configuration.

Various vehicle and sensor shields and other techniques have been tried to limit this problem. These include special heater control circuits and modified sensor shields. Such remedies typically increase vehicle or sensor complexity, adding to cost of production. Vehicle shields have met with some success but, when incorrectly designed, have actually made the problem worse.

Traditionally, the typical oxygen sensor shield design use holes or openings of a louvered shape along the sides of the shield to direct exhaust gas to the sensing element. These designs, although not complex, do not provide sufficient protection against water impingement to the sensor. More complex designs include modifications of the traditional louvered shield, e.g., employing a double walled shield with holes in the side, or holes in both the side and tip end of the shield.

A second problem associated with liquid water impingement upon the sensor has also been detected. If the ceramic sensing element becomes wetted, the time to heat it to operating temperature is greatly extended. The ceramic element typically operates at minimum temperatures of 300° C. to 400° C., depending on sensor design and requirements, for satisfactory function. Tests have shown that water impingement increases the time to operation by five times or more. A shield design that prevents water impingement will therefore reduce heating time and increase efficiency.

The shield must protect the fragile ceramic sensing element from mechanical damage, exhaust impact, and other foreign materials and contaminants while allowing entrance of a sufficient amount of gas to promote productive exhaust sensing.

BRIEF SUMMARY OF THE INVENTION

The drawbacks of the prior art are overcome by the gas sensor shield and method for manufacturing and use thereof. One embodiment of the gas sensor shield comprises: an elongated body comprising solid sides and a tip disposed across one end of said shield; and an opening disposed within said tip, wherein said opening comprises at least two elongated apertures.

One embodiment of the method for sensing gas comprises: exposing a gas sensor to a gas stream, said gas sensor comprising a sensing element in electrical communication with a wiring harness, wherein said wiring harness is disposed within an upper shell, and a shield disposed over at least a lower portion of said sensing element, wherein said shield comprises an elongated body comprising solid sides and a tip disposed across one end of said shield with an opening disposed within said tip, wherein said opening comprises at least two elongated apertures; passing gas through said opening to said sensing element; and determining the concentration of at least one component of said gas.

One embodiment of the method for manufacturing a gas sensor shield comprises: disposing a sensing element in electrical communication with a wiring harness, wherein said wiring harness is disposed within an upper shell; and disposing a shield over at least a lower portion of said sensing element, wherein said shield comprises an elongated body comprising solid sides and a tip disposed across one end of said shield, and an opening disposed within said tip, wherein said opening comprises at least two elongated apertures.

The above-described and other features will be appreciated and understood by those skilled in the art from the following detailed description, drawings, and claims.

BRIEF DESCRIPTION OF THE DRAWINGS

Referring now to the figures, which are meant to be exemplary, not limiting:

FIG. 1 is a perspective view of an exemplary embodiment of a gas sensor shield;

FIG. 2 is a cross-sectional view of a gas sensor employing one embodiment of gas sensor shield;

FIG. 3 is a frontal view along line 2—2 of the oxygen sensor shield of FIG. 1;

FIG. 4 is a cross-sectional view along line 3—3 of the oxygen sensor shield of FIG. 3;

DETAILED DISCLOSURE

Figure 5:
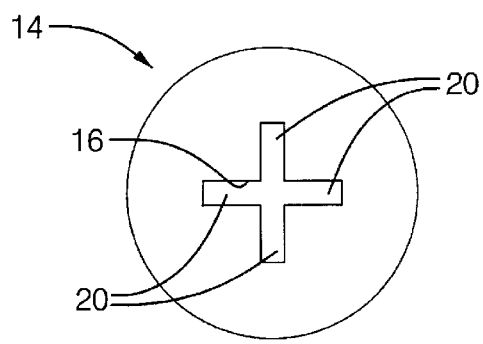
FIG. 5 is a frontal view of another embodiment of the oxygen sensor shield of FIG. 1.

The gas sensor shield is disposed over a portion of a sensing element in a gas sensor. The gas sensor comprises the sensing element disposed through a central body, lower shell, and the shield that connects to the lower shell. The opposite end of the sensing element is electrically connected to a wiring harness that can communicate with a vehicle when installed therein. During operation, the gas sensor is disposed in a gas stream with the sensing element in operable communication with the vehicle via the wiring harness. Gas in the gas stream enters the shield via the opening disposed in the tip thereof. Once in the shield, the gas contacts the sensing element that employs electrodes and an electrolyte to determine whether the gas is fuel rich, fuel lean, and/or the concentration of one or more components of the gas stream.

Referring to FIG. 1, a gas sensor shield is shown generally at 10 comprises a body 12 preferably having solid sides and including a tip 14 at one end. Body 12, which is preferably non-porous and aperture free, can comprise a single or multiple layer of heat-resistant material, such as ferrous materials (e.g., high temperature stainless steel or the like).

The body 12 and tip 14 of the shield 10, as shown in cross-section in FIG. 3, can be formed by any suitable processes, such as deep drawing, extrusion, welding, spin forming, and the like.

The shield 10, which is attached to an oxygen sensor (see FIG. 2) such as by welding, crimping, or the like, is installed in a position to cover at least a portion of the sensing element 80. Consequently, the shield 10 can preferably comprise a straight or flared open end 40 (see FIG. 4) capable of engaging lower shell 50. The general cross-sectional shape of the shield is based upon the shape of the sensor. Generally, a round (e.g., circular, oblong, and the like) and/or multi-sided (e.g., triangular, rectangular, square, trapezoidal, rectilinear, hexagonal, octagonal, pentagonal, and the like) cross-sectional geometry, with an elongated (e.g., cylindrical, tubular, semi-conical, inverted-conical, and the like) overall geometry possible.

When the sensor is installed in the exhaust of an internal combustion engine or other device, it is generally installed so that the exhaust gasses impinge against the shield 10 and sensing element in a direction approximately perpendicular to the axis (a) of the sensor. The gasses enter the shield 10 through opening 16 to contact sensing element. The opening 16 is disposed in the tip 14 and is defined by at least two slits 20. In other words, the exhaust gas does not flow from the exhaust stream directly through side holes in the shield and impinge on the sensing element 80 without contacting the shield. The exhaust gas must change flow direction, e.g., from a flow perpendicular to the axis (a) in order to enter the shield 10 and contact the sensing element 80. Not to be limited by theory, but as the exhaust gas changes direction (e.g., by contacting the shield), and enters the sensor through opening 16 that is designed to reduce particle and water entrance into the shield 10, particles are inhibited from contacting the sensing element. By disposing the opening 16 only within the tip 14, and not within the side 32 of the shield body 12, heavier constituents, like water and solid particles, will tend not to contact the element, while a sufficient amount of exhaust gas will be allowed to still reach the element. Therefore, the opening 16 is situated to prevent direct impingement of the exhaust gas and solid particles or water droplets on the element 80.

The opening 16 is configured to permit a restricted amount of exhaust gas to reach the ceramic sensing element (not shown). The opening 16 meters the amount of gas, which can reach the element to prevent an excessive amount that may swamp the element. The geometry of the openings 16 comprises two or more elongated apertures 20 (e.g., slits, holes, perforations, and the like, as well as combinations comprising at least one of the foregoing apertures) forming a "Y"-like or "T"-like opening in the tip 14 having a constant or variable width. Some possible geometries comprise a triangular, Y-like shape, T-like shape, star-like, two perpendicular lines, rectilinear, and combinations comprising at least one of the foregoing geometries. Some possible embodiments of the openings 16 are illustrated in FIGS. 3–11. For example, the opening 16 can have three slits of equal or different lengths radiating from a point that is substantially in the center of the tip 14. The slits may optionally be evenly displaced at 120° angles from one another and may partially extend to a curved portion 40 of the tip 14. The slits 20 can be formed by various shaped openings such as a series of holes or perforations (see FIG. 6), rectangular openings, multisided openings that may have a substantially constant (i.e., varying less than about 2% across the length of the aperture) width (see FIGS. 1, 3, 5, 7, 8, and 11) or a varied width (see FIGS. 6, 9, and 10).

The opening size is dependent upon the size of the shield curvature and its body diameter plus the length and width of each leg (aperture) of the opening. In one embodiment, the opening size can have apertures with a width of greater than or equal to about 0.25 millimeters (mm), with greater than or equal to about 0.5 mm preferred, and greater than or equal to about 1.0 mm more preferred. Also preferred is a width of less than or equal to about 2.0 mm, with less than or equal to about 1.5 mm more preferred. With respect to length, a length of greater than or equal to about 2.0 mm can be employed, with greater than or equal to about 2.5 mm preferred, and greater than or equal to about 3.0 mm more preferred. Also preferred is a length of less than or equal to about 5.0 mm, with less than or equal to about 4.0 mm more preferred, and less than or equal to about 3.5 mm even more preferred. For example, for a shield having an inner diameter of about 13.15 mm, and a tip curvature radius of about 4.76 mm, the apertures can have a size of about 0.5 mm×about 4 mm, with a size of about 1 mm×about 3 mm preferred. This configuration results in a small flat area on the tip of the shield, and a portion of the legs of the "Y" project up into the curve area.

In the tip 14, the opening 16 can be disposed centrally, emanating from axis (a) or off center, preferable toward the downstream location. Since the tip 14 can be flat and/or rounded, the opening 16 can extend into the curved area 30 of the tip 14, as is shown in FIG. 4, with limited extension into the curved area 30 preferred to prevent direct exhaust gas impingement on the sensing element 80. This shape tends to capture a metered amount of the exhaust gas and create turbulence that insures adequate exchange of gasses within the space between the sensing element 80 and shield 10 to prevent stagnation and excessive time lag (e.g., about 0.1 to about 0.3 seconds longer than the time lag for a sensor with louvered shield at 260° C. exhaust temperature to cross 450 millivolts (mV)) in measuring the gas.

Limiting the potential maximum length of the slits 20 to minimize the area of the opening 16, will subsequently reduce the projection of the slits 20 into the curved area 30 and will prevent direct impingement of materials against the element. However, insufficient opening area may potentially cause water to become trapped within the shield. To minimize this potential effect, the opening 16, preferably comprises a multiplicity of slits 20, preferably at least two slits. Employing at least two slits additionally provides for the drainage of water from at least one of the slits 20, should water or other materials get into the shield, which most often results when the shield is installed in a horizontal fashion, while allowing exhaust gas simultaneously access.

Despite the possibility for different configurations as described above, the opening 16 can be designed within a size range to attain optimum performance. An excessively small opening will slow the response of the sensor to changes in exhaust gas composition. Since the purpose of the sensor is to monitor these changes, excessive slowing will be detrimental to performance and confound the purpose of the sensor. Furthermore, excessively small openings are difficult to form on a mass production basis. On the other hand, an excessively large opening can be ineffective, defeating the purpose of particulate and liquid shielding. Balancing the size issues while controlling the amount of gas reaching the sensing element has been found to improve the sensor's accuracy. For instance, sensors similar to standard heated sensors but with louvered shields consisting of about $\frac{1}{6}^{th}$ the normal opening area were compared to "Y" hole shields with 1×3 mm legs, and to "Y" hole shields with 0.5×4 mm legs. During a perturbation type performance test run at 260° C. and a 1 Hz perturbation frequency, the response and lag were similar for the small louver and 1×3 "Y" configuration, but there was more slowing and lag for the 0.5×4 "Y" hole. At similar exhaust temperature but with a 0.5 Hz perturbation, both "Y" holes were significantly slower. The smaller "Y" caused the most pronounced effect in the lean to rich gas shift direction. The smaller "Y" hole caused the most significant shift of the sensor control point in the rich direction. While some rich shift is desirable, there was concern that the amount for the 0.5×4 "Y" hole might be excessive.

Figure 6:
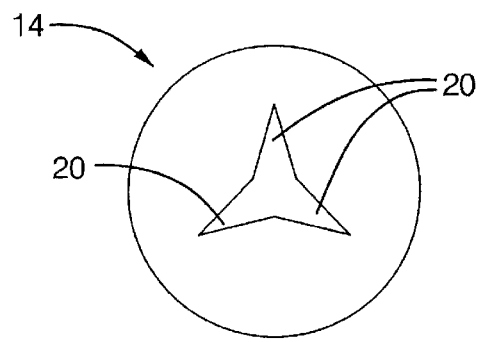
FIG. 6 is a frontal view of another embodiment of the oxygen sensor shield of FIG. 1.
Figure 7:
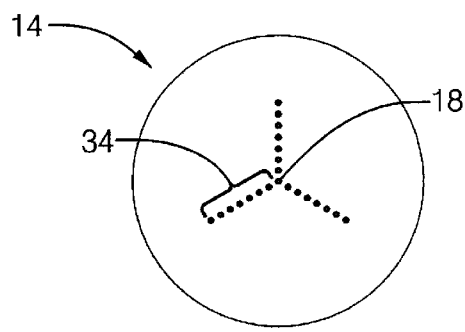
FIG. 7 is a frontal view of yet another embodiment of the oxygen sensor shield of FIG. 1.
Figure 8:
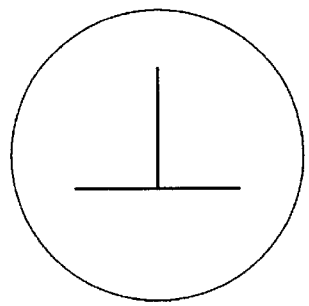
FIG. 8 is a frontal view of another embodiment of the oxygen sensor shield of FIG. 1.
Figure 9:
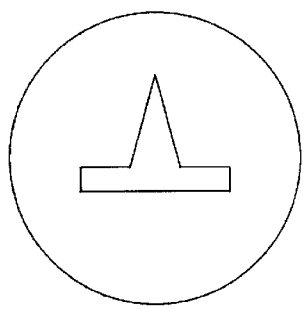
FIG. 9 is a frontal view of another embodiment of the oxygen sensor shield of FIG. 1.
Figure 10:
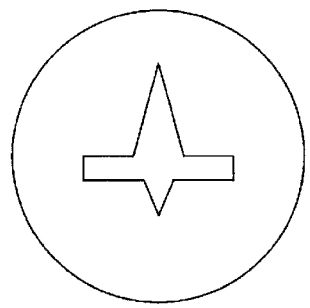
FIG. 10 is a frontal view of another embodiment of the oxygen sensor shield of FIG. 1.
Figure 11:
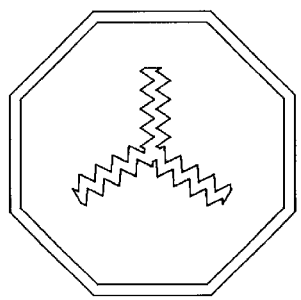
FIG. 11 is a frontal view of another embodiment of the oxygen sensor shield of FIG. 1.

Referring now to the Figures. FIG. 5 is a frontal view showing another embodiment of oxygen sensor shield. In this embodiment, the opening 16 comprises four slits 20, all generally rectangular in shape and equally spaced at about 90° angles from one another. Yet another embodiment of oxygen sensor shield is shown in FIG. 6. Here, the opening 16 comprises three slits 20, all generally triangular in shape and equally spaced at about 120° angles from one another. Optionally, additional slits could be added to this opening 16, rendering a star-shaped opening. Referring now to FIG. 7, another embodiment is shown, wherein the slits 20 comprise a series of holes 34 aligned and extending from the center 18 of the tip 14. All of these exemplary embodiments prevent direct impingement of exhaust gas against the sensor element, while allowing for drainage of water when necessary.

Testing to date has shown that for shields with an opening configuration as described herein, there is a significant reduction in sensitivity to hot ceramic elements being cracked by liquid water contact. For example, the sensors were heated with the internal heater for two minutes and then sprayed with water and air for two minutes. The test was repeated up to ten cycles or until element damage was detected. It must be remembered that this is a very severe test. On one test where the sensors were in the vertical position, all three louvered sensors broke on the first cycle of water exposure. With smaller louvers, one failed on the first cycle, one at the second cycle, and the last at the sixth cycle. All three 0.5×4 "Y" holes lasted 10 cycles. One 1×3 failed at the seventh cycle and the other two passed all ten. From this as much as a tenfold improvement can be extrapolated and there is a significant reduction or elimination of element water soaking causing increased time for sensors to heat up and become active.

During one test, where a quantity of water and air was sprayed on the sensors for two minutes, the following results were observed. All five louvered sensors exceeded 120 seconds of time to activity when heater power was applied. Without the water the "Time to Activity" for these sensors was about 40 seconds. (127 seconds was the limit of the test). By contrast, the "Y" hole sensors gave similar "Time to Activity" after the water exposure compared to the unexposed time. During the first exposure, the water was turned off before the heater was turned on. The "Y" holes were tested a second time using the same water exposure, but leaving it on after the heater was turned on. There was only minimal slowing of the time to activity. "Y" hole shielded sensors experienced minimal contamination of element surfaces by materials in the exhaust gas when compared to sensors with louvered shields. Silica fouling is used as the measure. Lean voltage increase is an indicator of silica fouling. After 50 hours exposure, standard sensors showed about 350 mV lean voltage and over 600 mV after 100 hours. By contrast, the "Y" hole sensors were at about 70 mV (within the 100 mV max spec) at 50 hours and at about 200 mV after 100 hours.

It should be noted that at low exhaust temperatures, the sensing element temperature of an internally heated sensor is increased by 30° C., to 50° C., compared to designs using louvers. At higher temperatures, the effect is on the order of 15° C. It can be extrapolated that there will be little temperature difference at very high exhaust temperatures.

In another test, "Y" hole shields were compared to louvered shields for water induced crack resistance, with the sensors mounted at a 4:00 degree insert angle. All of the sensors employed 18 watt heaters. Even at severe mounting angles, the "Y" sensor provided better performance with some of the sensors lasting at least 10 cycles, while the louvered shield sensors all failed by 9 cycles.

Compared to sensor designs with louvered slits and holes in the side of the shield, the embodiments described herein limit the amount of exhaust gas and exhaust "contaminants" which reach the sensor's ceramic element. This is achieved by keeping the primary flow away from the element by the position of the shield opening and by reducing the overall amount of exhaust gas touching the element with a smaller opening. Opening location and size control prevents such things as exhaust borne water from reaching the element and promotes improved catalysis of the exhaust gasses on the element surface. The preferred three-slit minimum of the opening provides an improved path for water egress.

While preferred embodiments have been shown and described, various modifications and substitutions may be made thereto without departing from the spirit and scope of the invention. Accordingly it is to be understood that the apparatus and methods have been described by way of illustration only, and such illustrations and embodiments as have been disclosed herein are not to be construed as limiting to the claims.

What is claimed is:

1. A gas sensor shield, comprising:
    an elongated body comprising solid sides and a tip disposed across one end of said shield; and
    an opening disposed within said tip, wherein said opening is defined by at least two elongated apertures radiating from a central point.

2. The shield of claim 1, wherein said tip has a geometry selected from the group consisting of rounded and dome-like.

3. The shield of claim 1, wherein the opening is defined by least three elongated apertures radiating from said central point.

4. The shield of claim 3, wherein said apertures have a width of about 0.25 mm to about 2.0 mm, and a length of about 2.0 mm to about 5.0 mm.

5. The shield of claim 4, wherein said width is about 0.50 mm to about 2.0 mm, and said length is about 2.5 mm to about 4.0 mm.

6. The shield of claim 5, wherein said width is about 1.0 mm to about 1.5 mm, and said length is about 3.0 mm to about 3.5 mm.

7. The shield of claim 3, wherein said apertures have a width of about 0.5 mm to about 1.5 mm, and a length of about 2.5 mm to about 3.5 mm.

8. The shield of claim 3, wherein said elongated apertures each have a geometry selected from the group consisting of triangular, rectangular, trapezoidal, square, and combinations comprising at least one of the foregoing shapes.

9. The shield of claim 3, wherein said at least three elongated apertures are disposed at 120° angles from one another.

10. The shield of claim 3, wherein said opening comprises at least four elongated apertures disposed at 90° angles from one another.

11. The shield of claim 1, wherein said opening has a geometry selected from the group consisting of triangular, Y-like shape, T-like shape, star-like, two perpendicular lines, rectilinear, and combinations comprising at least one of the foregoing geometries.

12. The shield of claim 1, wherein said apertures have a substantially constant width.

13. A method for manufacturing a gas sensor shield, comprising:
    disposing a sensing element in electrical communication with a wiring harness, wherein said wiring harness is disposed within an upper shell;
    disposing a shield over at least a lower portion of said sensing element, wherein said shield comprises an elongated body comprising solid sides and a tip disposed across one end of said shield, and an opening disposed within said tip, wherein said opening is defined by least two elongated apertures radiating from a central point.

14. A method for sensing gas, comprising:
    exposing a gas sensor to a gas stream, said gas sensor comprising a sensing element in electrical communication with a wiring harness, wherein said wiring harness is disposed within an upper shell, and a shield disposed over at least a lower portion of said sensing element, wherein said shield comprises an elongated body comprising solid sides and a tip disposed across one end of said shield with an opening disposed within said tip, wherein said opening is defined by least two elongated apertures radiating from a central point;
    passing gas through said opening to said sensing element; and
    determining the concentration of at least one component of said gas.

15. The method of claim 14, wherein said tip has curved area disposed in between the top of said tip and said body, wherein said opening is disposed within said curved area.

16. A gas sensor, comprising:
    a sensing element; and
    a shield disposed over a portion of said sensing element, wherein said shield comprises an elongated body comprising solid sides, a tip disposed across one end of said shield and an opening disposed within said tip, wherein said opening is defined by at least two elongated apertures radiating from a central point.

* * * * *